United States Patent [19]

DeVries et al.

[11] Patent Number: 4,759,750
[45] Date of Patent: Jul. 26, 1988

[54] PRESSURE SENSING SYRINGE

[75] Inventors: James H. DeVries, Grand Rapids; Richard J. VanPopering, Newaygo, both of Mich.

[73] Assignee: DLP Inc., Grand Rapids, Mich.

[21] Appl. No.: 944,193

[22] Filed: Dec. 22, 1986

[51] Int. Cl.[4] ............................................. A61M 5/18
[52] U.S. Cl. .................................... 604/121; 604/228; 73/864.16; 116/DIG. 17; 128/748
[58] Field of Search ............... 604/118, 121, 228, 218; 128/748, 672–675; 73/864.16; 116/272, 279, DIG. 17

[56] References Cited

U.S. PATENT DOCUMENTS 2,567,895  9/1951  Rommer ............................. 604/121
4,064,879 12/1977  Leibinsohn ......................... 604/121
4,624,659 11/1986  Goldberg et al. ................... 604/121

Primary Examiner—Dalton L. Truluck
Assistant Examiner—Denise Whelton
Attorney, Agent, or Firm—Barnes, Kisselle, Raisch, Choate, Whittemore & Hulbert

[57] ABSTRACT

A syringe for providing a tactile signal to a person who is directing a fluid to a vein of a patient, for local anesthesia administration where a specific infusion pressure should not be exceeded, and other uses where delivery pressure is critical. A biased pressure sensitive piston is interposed between the syringe plunger and an actuating thumb pressure element. When a preset pressure is reached in the syringe body, a projection reaches the thumb to alert the administering person that the preset pressure has been reached.

1 Claim, 1 Drawing Sheet

U.S. Patent
Jul. 26, 1988
4,759,750
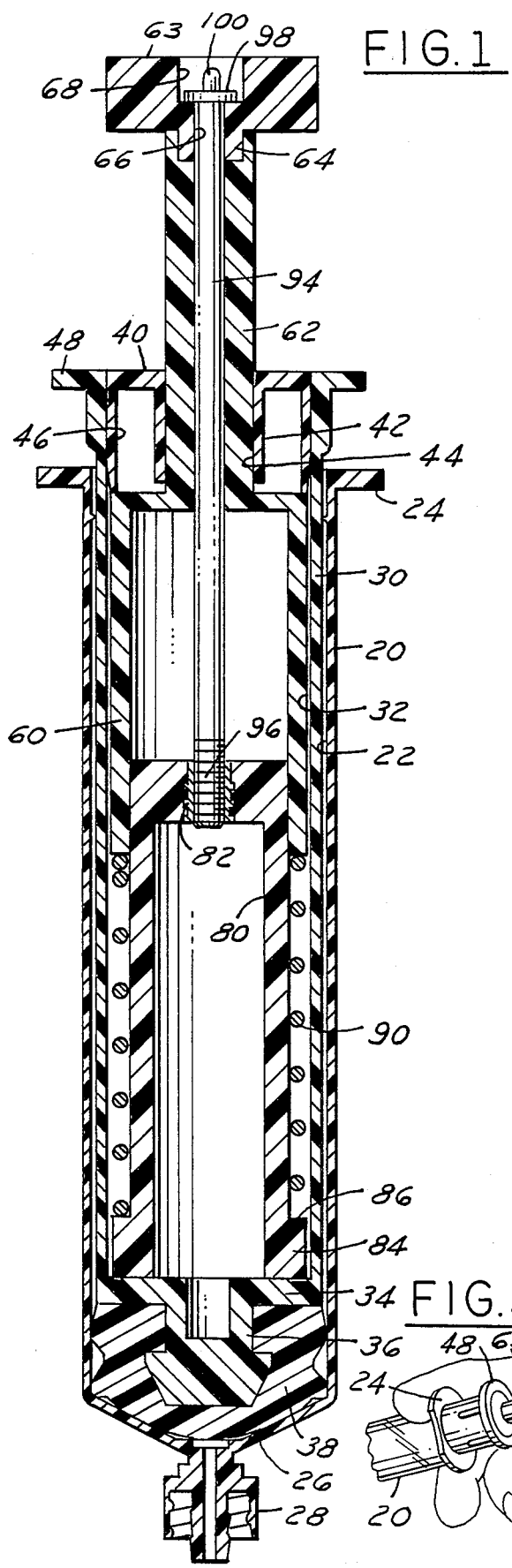
FIG. 1
FIG. 2
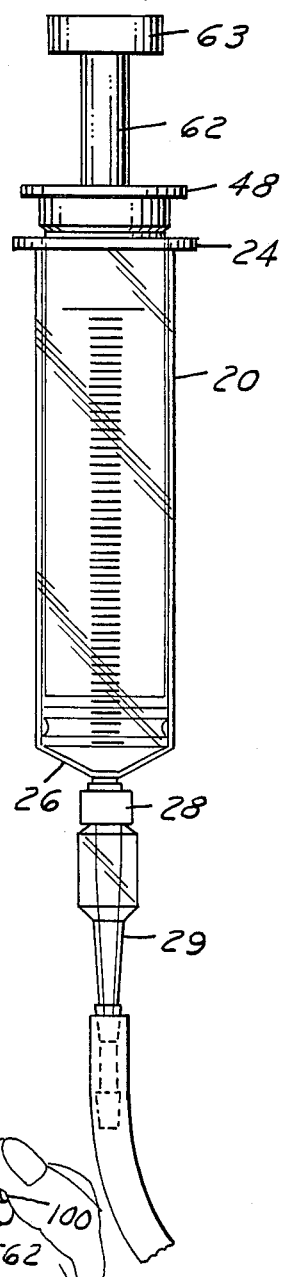
FIG. 3

PRESSURE SENSING SYRINGE

FIELD OF INVENTION

Syringe for use in distending autologous-vein preparatory to utilization as a by-pass graft in heart surgery, and other medical uses such as regional administration of anesthetic, and controlled inflation of balloon catheters.

BACKGROUND AND OBJECTS OF THE INVENTION

In connection with open-heart surgery, it is common to "harvest" a vein from the leg of the patient for use in a graft during the surgical process. Once the vein is removed from the patient, it must be distended by the introduction of a fluid, usually blood, to check the integrity of the vein as to leaks or other characteristics. In this process, it is very important that the testing be accomplished without overly distending the vein. A maximum pressure of 250 millimeters of mercury is desirable.

Excessive distention pressures during vein testing are known to affect adversely the endothelial covering and instigate progressively degenerative and regenerative changes throughout the layers, thus predisposing to early graft thrombosis or subintimal hyperplasia.

The testing is done by using a syringe which is filled with a predetermined quantity of blood and then a cannula connected to the syringe is inserted into one end of the vein and the other end is closed for the testing.

Other uses include the administration of local anesthetic to a tourniquetted area to prevent excusion beyond the desired area, and the inflation of balloon cuffs on a variety of cannulae and catheters.

It is an object of this invention to provide a syringe which can be manufactured to specific pressure limits and which has a tactile feedback to alert the surgeon when a certain pressure has been reached.

It is a further object to provide a distending syringe which is relatively inexpensive and which can be furnished in sterile condition and disposed of when the particular use is completed.

It is a further object to provide a syringe which can be manipulated with one hand and which signals the surgeon when a certain pressure is reached.

It is known to attach a stationary pressure gauge between the syringe and a cannula to monitor the pressure in the vessel as described in the Annals of Thoracic Surgery, Vol. 41, No. 5, May 1986, Page 569. Another vein distention system utilizes a balloon on the syringe to control the pressure in the vein (Bonchek-Shiley Vein Distentive System).

In the present invention a syringe plunger incorporates a spring-biased piston which is responsive to cannula pressure and which carries a stem projecting through the exterior plunger. The stem responds to movement of the piston and moves in contact with the surgeon's thumb to alert him to the set pressure limit.

Other objects and features of the invention will be set forth in the following description and claims in which the principles of the invention are set forth together with details to enable persons skilled in the art to practice the invention, all in connection with the best mode presently contemplated for the invention.

BRIEF DESCRIPTION OF THE DRAWINGS

Drawings accompany the disclosure and the various views thereof may be briefly described as:

FIG. 1, a longitudinal section of the syringe assembly.

FIG. 2, an elevation of a syringe showing the manner of use.

FIG. 3, a perspective view of the manner of using the syringe.

DETAILED DESCRIPTION OF THE PRINCIPLES OF THE INVENTION AND THE MANNER AND PROCESS OF USING IT

With reference to the drawings, a syringe body 20 has a cylindrical opening 22 and a standard flange 24 at the open end. The closed end 26 has an internally threaded fixture 28 for mounting a suitable cannula 29 having a threaded end which is to be inserted into the autologous vein and ligated or otherwise introduced for appropriate uses.

Within the syringe body 20 is a syringe plunger 30 with an interior cylindrical recess 32 and a closed end 34 with a flanged protrusion 36 to mount and carry a resilient sealing tip 38. The end of the plunger 30 opposite the sealing tip is closed by a double flanged ring 40 having an inner flange 42 surrounding a central opening 44 and outer flange 46 sealed in the end of the plunger 30 within a flange 48 by a suitable adhesive or welding process.

Within the syringe plunger 30 are two hollow pistons. The first piston has a cylindrical body 60 open at the interior end and an extended neck 62 terminating at a recessed end which carries a circular cap 63 having a small collar 64 secured to the neck 62 by a suitable adhesive or welding. The cap 63 has a central opening 66 enlarged at 68 in a recess open at the top of the cap.

The piston 60 has a clearance sliding relationship to the inside of plunger 30 and its outward motion is limited by the inner flange 42 of ring 40.

The second piston in the syringe plunger has a cylindrical body 80 slidable in body 30 of the first piston and closed at the top except for a threaded brass insert 82 molded into the head of the piston. A flanged portion 84 at the skirt end of piston 80 forms a shoulder 86 which provides a seat for one end of a stainless steel coil spring 90. The other end of the spring seats against the lower skirt edge of the piston 60. The upper end of the piston body 80 is slidably received in the piston 60.

A shaft 94 has a threaded end 96 which is adjustably received in the brass insert 82 of piston 80. The other end of the shaft extends through he neck 62 and has a small flange 98 which fits in the recess 68 or cap 63. At the outer end of the shaft is a small tip 100 which will serve as a tactile indicator to the surgeon. The small flange 98 can have a hexagonal shape to facilitate adjustment of the shaft 94 relative to the piston 80.

The parts above described, with the exception of the spring 90 and the insert 82, can be made as molded plastic elements of a suitable material well known in the art of syringe manufacture.

IN THE OPERATION

As an example of use in connection with heart surgery, an autologous vein is obtained from the patient by conventional open dissection using a long continuous incision or by closed subcutaneous technique and preserved in heparinized blood for two to three minutes. Before testing begins, larger tributaries are secured with suitable sutures such as merselene sutures and finer ones with prolene sutures. The distal end of the vein is ligated and a cannula attached to the syringe is inserted into the proximal end and ligated. Prior to the insertion of the cannula a quantity of fluid, sometimes blood, is introduced into the syringe.

The syringe is then used to introduce fluid into the vein to distend it and check for leaks and other characteristics relative to the intended use as a graft in open heart surgery. The spring 90 acting on the pistons 60 and 80 is preset for a perdetermined pressure as, for example, 250 millimeters of mercury. When this pressure is reached, the resistance against the syringe seal 38 will be exerted on the piston 80 and spring 90. Thus will cause the shaft 94 to shift in the neck 62 and the indicator 100 will move out of recess 68. When the syringe is held as shown in FIG. 3, with the forefinger and middle finger below the syringe body flange 24 and the thumb on the cap 63, the surgeon will feel the projection 100 as it moves out of the recess 68 and he will know that he has reached the predetermined set pressure. At this point he may decide to go beyond this pressure depending on certain variable factors which he can observe. However, he will have been alerted by the tactile signal as to reaching set pressure. The set pressure can be predetermined by rotating the threaded shaft 94 to shift it axially of the piston 80.

The syringe body 20 can be graduated in a standard fashion to measure the fluid quantity introduced by retraction to the plunger 38. Indices may also be applied to the neck 62 to register the preset of the spring.

What is claimed is:

1. A syringe combination for use in distending autologous veins preparatory to use in open heart surgery and other medical procedures to provide tactile indication of pressure limits where cannula pressure is critical which comprises:
   (a) a syringe body for use with a cannula,
   (b) a first plunger movable on said syringe having an outer end and an inner end with a seal to draw in and force out fluid to be introduced into a vein,
   (c) a first means to actuate said first plunger positioned adjacent said first plunger and biased to an initial position axially outward of said first plunger,
   (d) a second means adjacent said first means biased against the first means and having indicator means within said first means to project axially outwardly of said first means when said bias is overcome by pressure on said first means resisted by said first plunger,
   (e) said first plunger being hollow, said first means being a second plunger within said first plunger biased by resilient means axially toward the outer end of said first plunger and having an outer projecting end to actuate said second plunger and said first plunger through said resilient means, and said second means comprises a third plunger biased against said first plunger, and
   (f) said second plunger having a neck portion projecting axially from said first plunger, and said third plunger having a shaft projecting into said neck portion toward the outer end thereof, said shaft being movable out of said neck portion when cannula pressure on said first plunger overcomes said biasing resilient means.

* * * * *